United States Patent [19]
Finholm

[11] Patent Number: 4,774,868
[45] Date of Patent: Oct. 4, 1988

[54] PIANO KEY ACTION

[76] Inventor: William S. Finholm, 640 Riverside Dr., Apt. 8A, New York, N.Y. 10031

[21] Appl. No.: 114,717

[22] Filed: Oct. 30, 1987

[51] Int. Cl.4 ..................... G10C 3/22
[52] U.S. Cl. ..................... 84/239
[58] Field of Search ..................... 84/236, 237, 239

[56] References Cited

U.S. PATENT DOCUMENTS 2,156,913 5/1939 Finholm ..................... 84/239
2,540,871 2/1951 Finholm ..................... 84/239

*Primary Examiner*—Lawrence R. Franklin
*Attorney, Agent, or Firm*—William T. Hough

[57] ABSTRACT

In a piano normally of a grand piano type, a key action mechanism includes a combination of a fly lever distal end acting on a hammer lever through an intermediate thrust balancing lever, the thrust balancing lever being pivoted at an intermediate portion between proximal and distal ends thereof, and the thrust balancing lever distal end having a change-of-direction roller over which a non-resilient cord is drawn, one end of the cord being connected to an intermediate portion of a wippen lever pivoted at one end thereof, and an opposite end of the cord being connected to a proximate end of a helical spring, and a distal end of the helical spring being connected to an intermediate portion of the fly lever of which the fly lever's lower portion is pivotably mounted on a distal end of the wippen lever, such that when an upward portion of a laterally-extending proximal end of the fly lever is raised to contact an abutment, further raising of the wippen's distal end moves the thrust balancing distal end upwardly as a result of the fly lever's distal end pivotally moving laterally from beneath the thrust balancing lever's distal end, downward pressure on the change-of-direction roller increasing as the fly lever's distal end pivots laterally.

10 Claims, 3 Drawing Sheets

PIANO KEY ACTION

This invention relates to a mechanism for improving piano keyboard key action, especially as a part of grand or concert pianos.

BACKGROUND

There have been numerous different types of mechanisms employed in piano key action. As is well known in the trade, the term "key action" and mechanism thereof refers to the mechanical chain of levers and combinations of levers which result in ultimately the piano key-hammer(s) striking the piano string(s) as the pianist plays on the keys. Additionally, however, it refers to the extent to which there is ease or alternately difficulty, sensitivity or alternately lack of sensitivity, to the force utilized in striking the piano key(s). It is noteworthy that the employment and use of a piano "soft pedal" of a piano reflects the recognition of lack of sensitivity of key action. Mere key action has in the past made it impossible to effectively or adequately play (strike) a key with varying degrees of force or touch as to obtain desired expression such as pianissimo, in playing a musical composition on the piano keys. The soft pedal when utilized, shifts the entire piano carriage and/or keys relative to position(s) of the piano string(s) such that the hammer(s) strike fewer strings for the same note—with a resulting softness (less loud) because fewer strings have been struck. The soft pedal approach amounts to all or nothing logic.

In conventional grand piano arrangement, with regard to a pivoted fly lever pivotably mounted on a distal end of a pivoted wippen lever, a fly lever's distal end freely passes through a space defined between forks, spaced-apart flanges, in a distal end of a thrust balance lever, with the fly lever's distal end being directly in contact with and supporting solely a lower face of an abutment mounted on a lower face of an intermediate portion of a pivoted hammer shaft. That arrangement is such that pivotal sideward movement of a fly lever's distal end from a supporting position and state beneath the pivoted shaft's abutment, results in the hammer-shaft lever abutment abruptly jerking downwardly while substantially concurrently a fly lever's distal end is impelling upwardly the hammer-shaft lever; when a hammer shaft lever abutment snaps downwardly as a result of the final full pressing downwardly on a piano key's proximal end, taken with movement of a fly lever's distal end from its supporting position, thereafter (until a full total repeat/return movement of all levers after release of downward pressure on the piano key's proximal end) the hammer-shaft's abutment comes to rest on an upper surface of spaced-apart flanges of the thrust balance lever. In that type of arrangement of elements, prior to the fly lever's distal end totally slipping from its supporting position, further upward movement of the distal end of the thrust balance lever has been thwarted by stop-structure. Accordingly, as a result of the thrust balance lever having been pivotally mounted at an intermediate portion thereof onto the wippen lever, the blocked further upward movement of the thrust balance lever's distal end causes the proximal end of the thrust balance lever to tend to move upwardly against downwardly-biasing stress of a tension spring, with a resulting increasing build-up of stress and tension. Accordingly, when the distal end of the wippen lever's distal end moves upwardly, driving upwardly the fly lever pivotally mounted thereon, the distal end of the fly lever by the above-noted increasing force and tension, increased pressure of the upper-end face of the fly lever is further caused to increase tension and stress as a result of the ever-increasing pressure of the fly lever's distal end against the lower face of the hammer-shaft's abutment. Eventually, as a result of continually increasing pressure and upward speed of movement of the fly lever's upper-end face, the pivoted hammer shaft is thereby caused to pivotably flip-upwardly as concurrently the excessive pressure, taken together with lever action of a lower proximal end of the fly lever against an abutment mounted on the support structure, causes the fly lever's upper-end face to sidewardly pop-out from beneath the hammer-shaft abutment's lower face. The above-described mechanism and action results in a high degree of friction, and action involving forceably popping-out or snapping-out from its supporting position. As a result of this type of action, it is virtually impossible to effectively vary the extent of jerking-action with any appreciable degree of sensitivity. This is to say, there is always the area of lack of control as a result of the inherent mechanism of that type of key action mechanism. Except for the extremes of lightly touching a piano key's proximal end during playing the piano, as opposed to pounding (with great force striking) the key, together with the use of a soft pedal to soften the intensity of key string sound when the string(s) are struck, expressions of intermediate degrees of loudness or softness have been substantially impossible. A typical patent illustrating a mechanism of this general type is the present inventor's U.S. Pat. No. 2,540,871 dated Feb. 6, 1951. The typical and more expensive and elegant grand pianos such as the Steinway pianos, embody the mechanism discussed in this paragraph.

In another type of key action mechanism as is typically shown and represented in the present inventor's Finholm U.S. Pat. No. 2,156,913 dated May 2, 1939, the distal end of the fly lever supports solely the lower face of the distal end of the thrust balance lever, and solely the thrust balance lever distal end's upper face supports the lower face of the hammer shaft abutment. The remaining mechanism of this 1939 patent is otherwise considerably different from the mechanism and structure of the 1951 patent and from that of the present invention.

In the Steinway and other similar grand pianos, there are two separate leaf springs employed, mounted on the wippen lever. One leaf spring—as above-noted, biases upwardly the thrust balance lever distal end against the above-noted "stop", relative to the wippen lever on which the thrust balance lever's distal end is mounted, as it moved upwardly. The thrust balancing lever's intermediate portion is pivotally mounted on the intermediate portion of the pivotally-mounted wippen lever. The other leaf spring biases the fly lever's distal end toward the position at which the fly lever distal end supports the hammer lever abutment. There are competing and counter-productive forces in operation in such prior art key action-arrangement. As a result of the return-action biasing on the fly lever, greater upward force of the fly lever's distal end against the hammer-shaft's abutment is required prior to the fly-lever's distal end popping-out from its support position. Once the "stop38 comes into operation, this also amplifies the great magnitude or intensity of the jerking-action when the fly lever's distal end snaps from beneath the hammer-shaft abutment. Also, in order to achieve sufficient thrust against the hammer-shaft's abutment to effectively propel the hammer with sufficient force against the piano string(s), it is required the fly lever have a relatively long dimension, there being a minimal length at which it would effectively operate. Likewise, in the mechanism above-described for the Steinway type arrangements, the "stop" that initiates the stress eventually leading to the fly lever's distal end popping-out from beneath the hammer-shaft's abutment, results in greater stress as length of the fly lever employed is increased. Such great stress inherently is present during the key action as a result in part, of the essential long fly lever, taken together with the "stop" that prevents further upward movement of the thrust balance lever's distal end. As above-noted, the ultimate result in that type of arrangement is a lack or loss of control of sensitivity to the "touch"—with regard to softness or loudness, when the key(s) are struck. The high tension necessitated prior to the fly lever's distal end snapping-out from its supporting position of and from beneath the pivoted hammer-shaft abutment, tremendously increases the amount of friction between the fly lever distal end and the lower face of the hammer-shaft abutment. Accordingly, this friction point has always been a most objectionable feature in a piano artist's attempting to play pianissimo, for one either pressed the key too far or not far enough, being hindered by friction during release of the fly lever's (jack's) distal end and pressurized resistance of the repetition drop screw—i.e. the above-noted stop. Also, because of the undesired large amount of friction and the wear and tear associated therewith, the life of a particular adjusted mechanism is extremely short, the mechanism being hypersensitive to such wear and tear; the result is frequent and recurring breakdowns—right up to and during concerts on the piano, apart from the inherent lack of control and lack of sensitivity always experienced by the pianist.

OBJECTS OF THE INVENTION

Accordingly, objects of the invention include the avoiding and/or overcoming one or more of the problems of the types discussed above.

Another object is to obtain an improved piano key action mechanism and operation thereof permitting sensitive and controlled execution of pianissimo and other variations of touch.

Another object is to obtain an improved piano key action mechanism making possible the above-noted sensitivity in effecting pianissimo and other variations of touch, by a novel mechanism of improved action flexibility and diminished friction and stress and/or dimished or eliminated sudden release of stress that characterized prior key action systems.

Another object is to obtain an improved piano key action combination achieving one or more prior objects, together with reducing friction in the operation thereof, sufficiently to avoid wear and tear associated with prior key action systems discussed above, and likewise to thereby decrease frequency of breakdowns.

Another object is to obtain a novel key action mechanism embodying a novel combination by which pressure moving friction-causing parts away from one-another, increases as degree of key movement progresses during the stroke of a key.

Another object is to obtain a novel key action mechanism embodying simplicity of combination and operation, together with improved and enhanced quietness thereof, while retaining essential free and fast repeating action during operation.

Another object is to improve piano tone by virtue of improved piano key action and repeat action, with regard to speed and freedom and ease of movement, together with sensitivity of the piano key to obtain a hammer stroke by touching or striking a key.

Another object is to obtain a novel piano key action combination eliminating or obviating dependence on the need for a soft pedal.

Another object is to obtain a novel piano key action combination of simple manufacture maintenance characteristics, that can be produced and maintained at low cost economically and time-wise.

Another object is to obtain a novel piano key action combination, which by virtue of its functional achievements, makes possible a piano of fewer and smaller parts.

Other objects become apparent from the preceding and following disclosure.

One or more objects of the invention are obtained by the invention as described herein.

BROAD DESCRIPTION

The present invention is an improvement combination providing achievements and advantages never before known nor possible in any piano, particularly in grand pianos. As set forth above, the invention relates to piano key action and mechanism thereof, and more particularly for pianos as follow. Such a piano typically of conventional structure and shape having base structures for the support thereof and for the mounting of piano strings and piano keys and lever and other structure conventional for the striking of the strings of a piano. The structural mechanism includes, among other things, a balancing rail and a plurality of piano keys pivotally mounted thereon in the conventional fashion. The conventional keys each has its proximal and distal ends, with the intermediate portion thereof pivotally mounted and adapted for the distal end thereof to press and move upwardly a pivoting portion of a wippen lever of which a proximal end thereof also is mounted on the support structure, when a proximal end of the key is struck or pressed downwardly. Pivoted on an intermediate portion of the wippen lever is a pivotally mounted thrust balancing arm pivoted at an intermediate portion of the thrust balancing lever, with an upper face of a distal end of the thrust balancing lever being supportable of an abutment of an intermediate portion of a piano hammer's shaft. The piano hammer shaft also has its proximate end mounted on the support structure. Also mounted on the distal end of the wippen lever is a fly lever of which an imtermediate portion thereof is mounted. A distal end of the fly lever extends upwardly and is supportable of the thrust balancing lever's distal end. A lower portion of the fly lever extends laterally or sidewardly sufficiently to eventually engage and abut an abutment member mounted on the support structure, when the distal end of the wippen lever is caused to rise as a result of striking or pressing downwardly on the key. Upon engagement of the fly lever's proximal end with the abutment, continued upward movement of the distal end of the wippen lever as the proximal end of the piano key is pressed downwardly, causes the distal end of the fly lever to move laterally away from its supporting position and state.

The improvement includes the above structures and arrangements thereof, in a novel inventive combination with each other and other members as follow. The upper surface of the distal end of the thrust balancing lever directly supports and drives upwardly the hammer-shaft abutment, as the upper distal end of the fly lever contacts and upwardly drives a lower surface of the thrust balancing lever's distal end. The distal end of the fly lever is preferably sufficiently squared or flanged (irregularly-shaped) that when the squared portion or flange (irregularly-shaped portion) further drives upwardly, the thrust balancing lever's distal end continues upward movement (as the fly lever's distal end continues to move laterally away from its supporting position after the proximal end of the flylever has abutted the abutment as the wippenlever continued to rise as the key's proximal end is pressed further downwardly). Mounted between a point on the fly lever with that point spaced-away from the location of its pivot, an elongated resilient member extends toward and is connected to the thrust balancing lever's proximate end sufficiently that the thrust balancing lever's distal end is caused to continue to move upwardly as the fly lever's distal end moves laterally away from its supporting position; that lateral movement away is principally a result of engagement of the fly lever's proximal end with the abutment that is mounted on the support structure.

More preferably the elongated resilient member in order to achieve optimal operation (as based on extension experimentation) critically includes substantially non-elastic cord (or line or the like) such as preferably Nylon thread, of which a distal end thereof preferably is connected to a preferably and critically necessary (for more optimal operation and functioning) helical spring, and a proximal end thereof is connected to the wippen lever at a point spaced-away from the wippen lever's location of pivotal mounting onto the base support structure; as a result of this arrangement, as the wippen lever continues to rise after the fly lever's distal end has engaged the support-mounted abutment, the angle of resultant pressure by the resilient member on the thrust balancing lever's proximal end defines a broader angle relative to the point of mounting of the elongated resilient member's proximal end, and an equal broader angle relative to the point of mounting on a distal end of the elongated resilient member. Consequently, there is a continuing decrease in the downward speed of movement of the proximal end of the thrust balancing lever, initially as rapid movement and thereafter slowing movement sufficiently to cause the thrust balancing lever's distal end to continue to rapidly initially move upwardly to diminish pressure and/or frictional contact with the sidewardly moving fly lever's distal end, as the distal end of the wippen lever continues to rise while the proximal end of the piano key continues to be pressed further downwardly. The effect of this is to diminish frictional contact between the upper distal end of the fly lever as the fly lever distal end moves laterally away from its supporting position. The accentuated upward movement thereby provided to the distal end of the thrust balance lever together with the accompanying support thereof by virtue of the elongated resilient member acting on the thrust balance lever's proximal end, serves to result in greater force acting to drive upwardly the pivoted hammer-shaft such that the the hammer forcefully strikes the piano string(s). Additionally, the reduced frictional pressure of the thrust lever's distal end on the upper surface of the fly lever's distal end, facilitates easy jerk-free movement of the fly lever's distal end laterally from its prior supporting position and state. Reverse-direction movements and above-described angles, by the same laws of lever-physics, serve to facilitate a rapid and effective return in the fast repeat action for the key and above-described levers.

In a further preferred embodiment, there extends a rapid elongated lever having its proximal end rigidly mounted on the fly lever at a point spaced-away from the pivot point of the fly lever. The lever extends toward the elongated resilient member, and is positioned such that lateral movement of the fly lever distal end away from its supporting position (after engagement of the fly lever's proximal end with the support-mounted abutment) causes upward movement of the rigid lever's distal end. The distal end of the elongated resilient member, preferably the proximal end of the helical spring thereof, is caused to move concurrently immediately upwardly thereby increasing stress on the resilient member. The increased stretching stress causes the downward force on the wippen lever's proximal end to be even greater, further accentuating the upward lift and speed thereof for the wippen lever's distal end.

In a further preferred embodiment, the distal end of the wippen lever includes a change-of-direction member, such as a roller or a spool or a pulley structure. The change-of-direction member is positioned and mounted such that the helical spring or preferably the non-resilient cord moves by traveling on a rolling surface of the change-of-direction member. This rolling movement further prevents or avoids frictional resistence and further provides for smooth non-jerky and easy movement of the entire key action.

The invention maybe better understood by making reference to the following Figures.

THE FIGURES

FIG. 1 diagrammatically illustrates an in-part side view of a piano inner works inclusive of the support structures and levers and hammer and strings constituting the essential parts or elements of the present invention with regard to piano key action and repeat-return.

FIGS. 2A through 2D diagrammatically illustrate the same embodiment as that of FIGS. 1, in a corresponding same side view, but at progressive stages of movement during key action as the piano key is played by a performer, shown in partial cut-away view of piano supporting structures.

DETAILED DESCRIPTION

For all Figures, the same embodiment is disclosed, differing solely in the FIGS. 2A through 2D representing various stages before and during key action activation and functioning. Accordingly, except for the Figures showing different positions of the levers, with correspondingly different angles of movements and as shall be identified below, all indicia of the FIGS. 2A through 2D will be the same or similar to those of FIG. 1, to the extent that there is repetition of identification.

Figure 1:
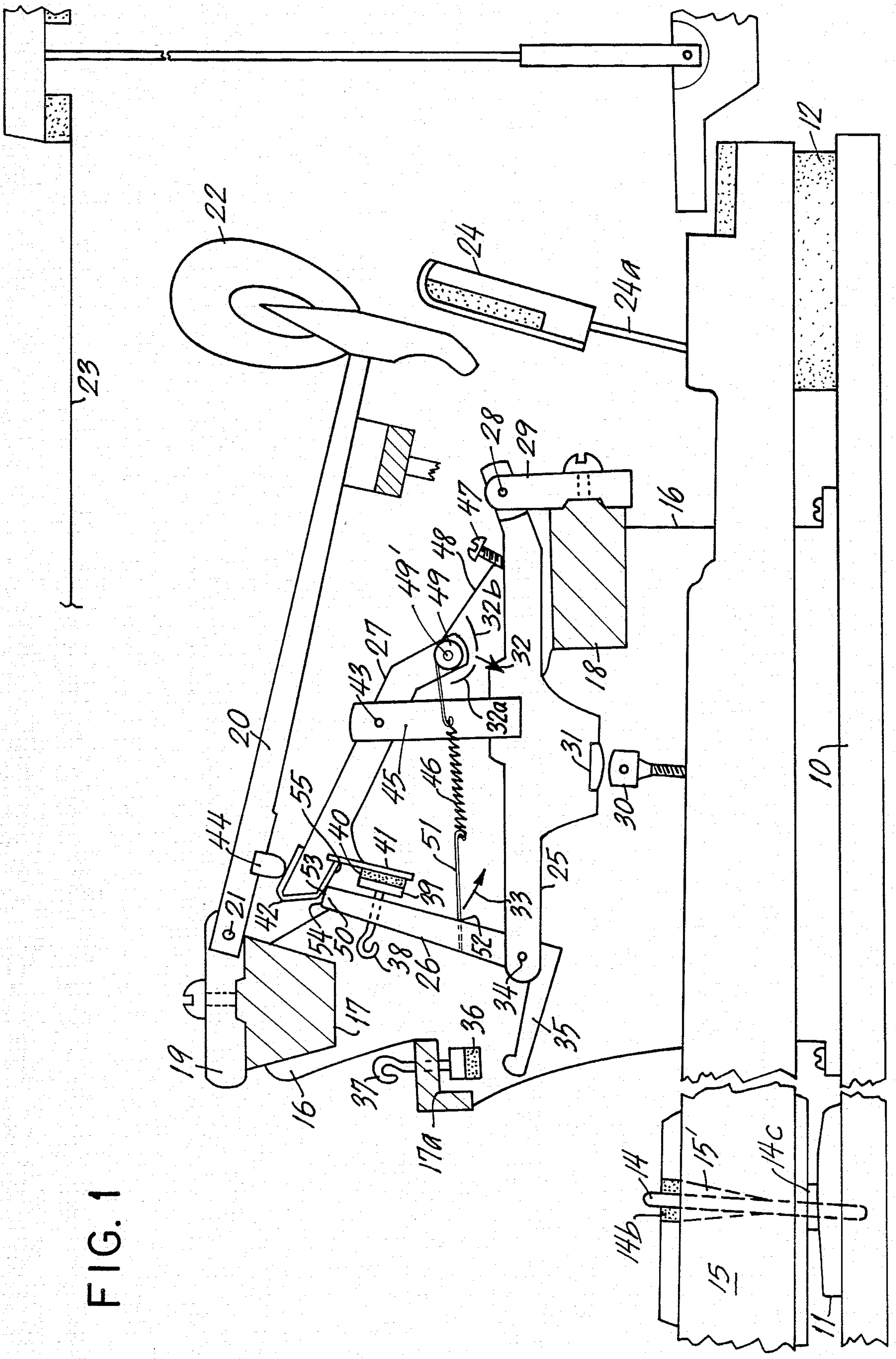

Thus, all indicia identified in FIGS. 2A through 2D will be found in FIG. 1, except for the above-noted exceptions.

Making reference to FIG. 1, there is disclosed the key frame 10 of typically a baby grand piano—i.e. the basic piano support structure on which other items are mounted. On that key frame 10 is mounted a balance rail 11, which is supplemental support structure. The piano key 15 is mounted on a key balancing pin 14, with the balancing button 14*a* in place around the balancing pin 14. At a distal end of the key 15, there is a supporting key-rest 12, further support structure, with the proximal end of a key which conventionally would be guided by a conventional guide pin (not shown). Top and bottom support structures above and below the key, form aperture space **14*b*, aligned with the key's aperture space 15′through which pin 14 is mounted. There is additional support structure cumulatively referred to as 16 (shown in two different places) that is mounted on the support structure 10, directly or indirectly. A further support member 17 (a rail), mounted on support structure 16 has mounted thereon a hammer base member (hammer shank flange) 19 on which the hammer-shaft 20 is mounted at its proximal end on pin 21, having hammer 22 at its distal end, positioned to strike string 23 when the proximal end of the key 15 is struck (played). An intermediate portion of the hammer-shaft 20 has the abutment 44 mounted on the underside of the hammer shaft 20. Shaft 24*a* carried the back check 24 for checking the downstrike of its related hammer 22**.

The additional support structure 18 (another rail) has mounted thereon the wippen base (flange) 29 on which pin 28 pivotally mounts wippen lever 25 having rest-member 31 by which the wippen lever 25 rests on support member 30 mounted on the key 15. Fly lever 26 is mounted by pin 34 on the distal end of wippen lever 25, and thrust balancing lever 27 is pivotally mounted by pin 43 on thrust balancing lever support 45 that is rigidly mounted on an intermediate portion of the wippen lever 25. Roller 49 is mounted by pin 49′ on the proximalend of the thrust balancing lever 27. Elongated rigid member (rod) 51 is mounted at location 52 on and extends laterally from an intermediate portion of the fly lever 26, extending toward the roller 49, and has connected to a distal end of the fly lever 26 the distal end of helical spring 46. The proximal end of spring 46 is connected to the distal end of non-flexible cord 48 which is secured to screw 47 screwed into a proximal end of the wippen lever 25.

A leather covering-pad 42 is mounted on a distal end of the thrust balancing lever 27, and also stop-member 41 is mounted on the distal end of the thrust balancing lever 27, with a padded head 39 being mounted by adjustable screw-like mount-member 38 mounted through the distal end of the fly lever 26.

Fly lever distal end 35 has stop-abutment 36 mounted on adjustable screw-type member 37 with the stop-abutment aligned with the distal end 35 such that the fly lever distal end 35 will come into contact with and abut stop-abutment 36 when the proximal end of the piano key 15 is pressed. The screw-like member 37 is mounted in support rail **17*a* (as a further part of the additional base support structure 16**, mounted thereon).

Pressure of the cord 48 on the roller 49 acts with a resultant force-vector 32; the angle **32*a* is defined between the distal ends of the cord 48 and the resultant force vector 32. Likewise, the angle 32*b* is defined between the proximal end of cord 48 and the resultant force vector 32. Angle 32*a* is always substantially equal to angle 32*b* because the force exerted through opposite proximal and distal ends of the cord 48 is equal, and the resultant force vector 32 is the vector of the force on the roller 49 and its mounting pin 49′, which force or pressure is transmitted to the proximal end of the thrust balancing lever 27**.

The resultant force vector 32 results from the retraction force of helical spring 46 acting on the distal end of the lever 51.

Figure 2A:
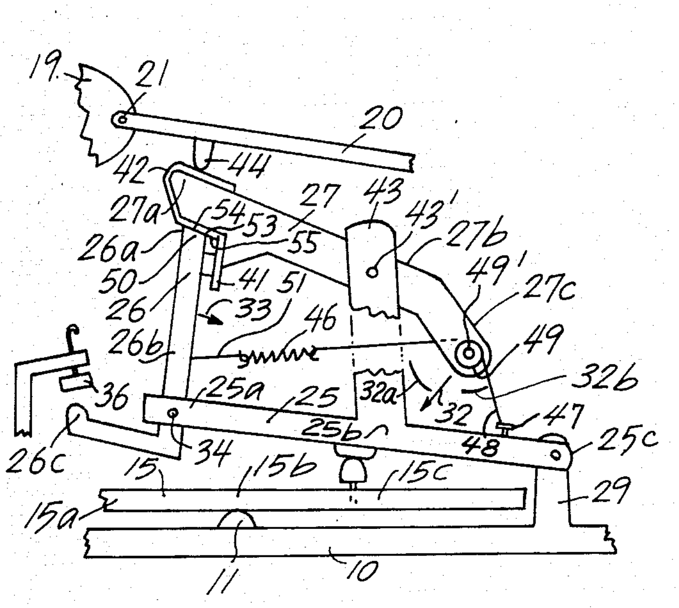

With regard to FIGS. 2A through 2D, the functioning of the key action and repeat action of the invention is illustrated. The Figure 2A represents the state existing prior to a pianist striking (pressing downwardly) the proximal end of the key 15, such that angles **32*a*′ and 32*b*′** are each at their smallest number of degrees.

Figure 2B:
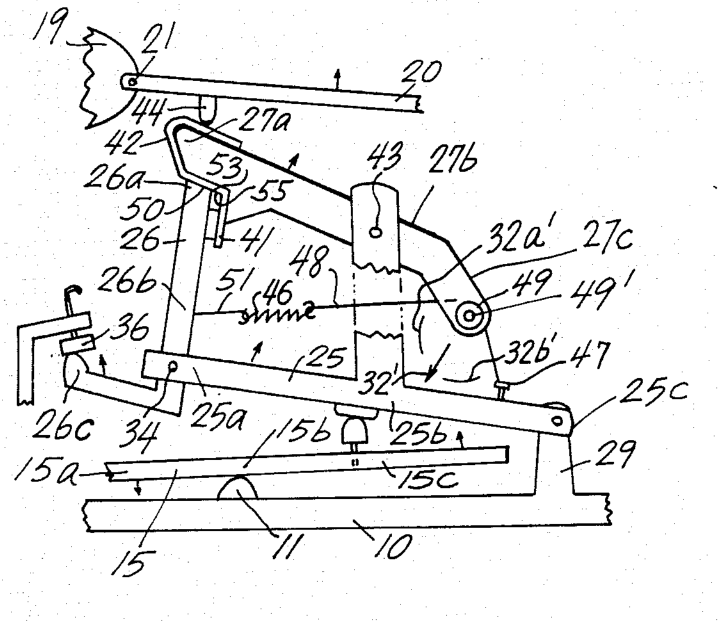

FIG. 2B represents the state when the proximal end of the key 15 has been pressed downwardly (by the striking thereof) sufficiently for the fly lever distal end **26*c* to come into contact with the stop-abutment 36 as a result of the wippen lever's distal end 25*a* having been lifted pivotally, together with the lifting (upward movement) of all structures mounted on the wippen lever 25. The number of angle degrees in each of angles 32*a*″ and 3*b*″ is the same as the number of degrees in each of the angles 32*a*′ and 32*b*′, because there has not been any pivoting action of the thrust balancing lever 27*b*** thus far.

Figure 2C:
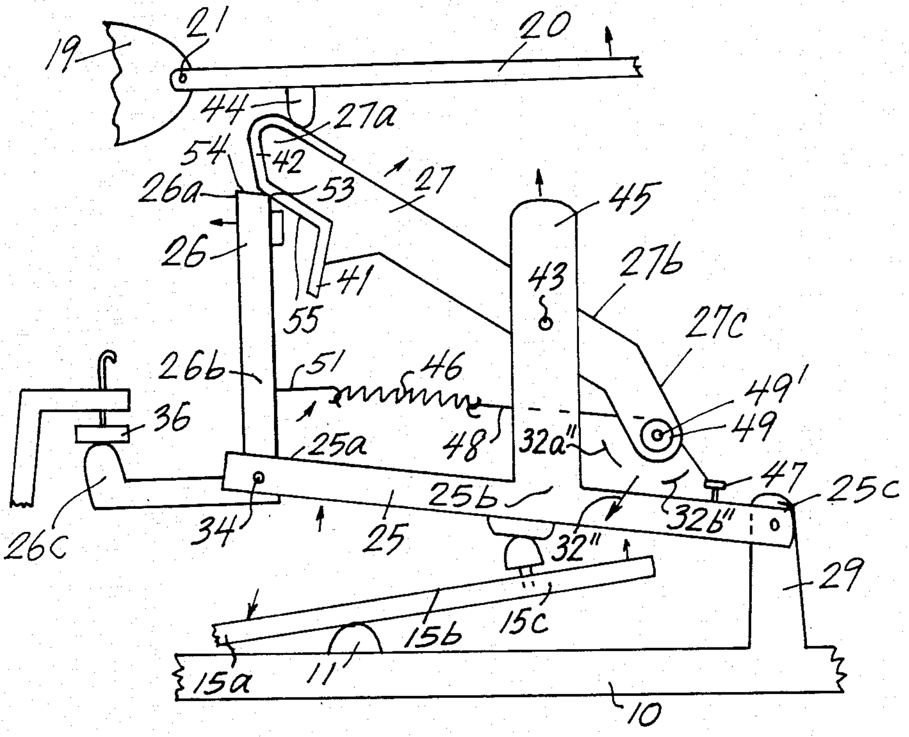

FIG. 2C illustrates the state when the proximal end of the key 15 has been further depressed (by the continuation of the striking thereof) as compared to the FIG. 2B state, whereby the wippen lever has been further raised together with the mounted support 45 mounted on the wippen lever, and together with thrust balancing lever 27. Because the fly lever's (26) distal end 35 has previously abutted the stop-abutment 36, the fly lever has begun to pivot the fly lever proximal end 54 from beneath the thrust balancing lever distal end **27*a* (and along face 55 of the leather pad 42), by which solely the squared corner 53 (of the fly lever's distal end 54) is the sole remaining frictional contact with the leather pad 42, and whereby the squared corner 53 presses upwardly an additional distance the thrust balancing lever distal end 27*a*, while concurrently the elongated rigid member 51 and its serially-attached helical spring 46 and the serially connected cord 48 act on the roller 49 with pressure to produce resultant force vector 32 also contributing to the lifting of the thrust balancing lever distal end 27*a*** to the illustrated position and state.

Figure 2D:
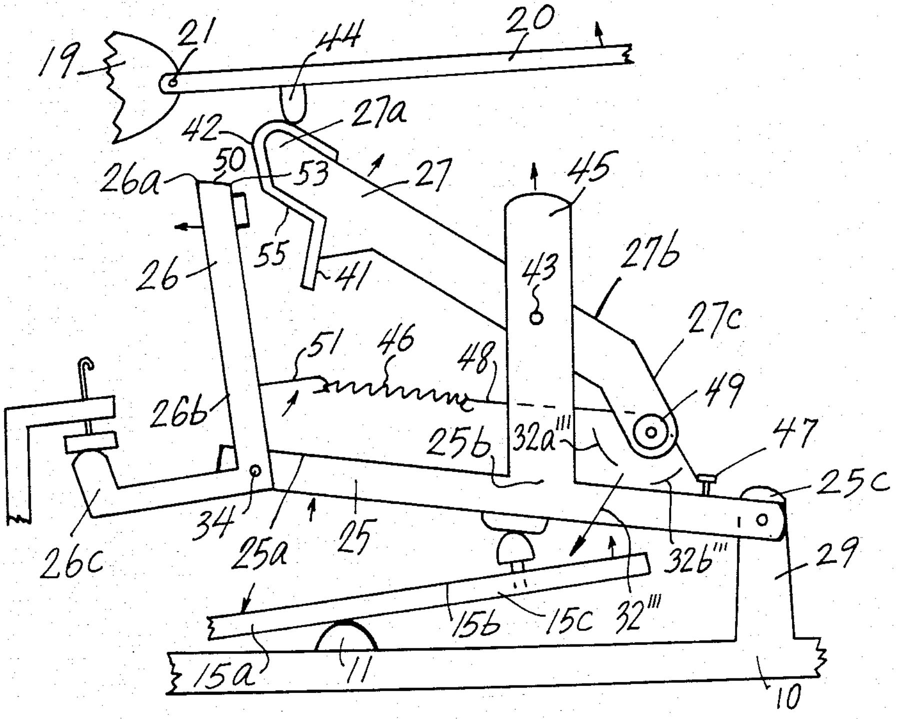

The FIG. 2D illustrates a still further downward movement of proximal end of the key 15 in the state of maximum depression thereof, whereby the continued movement of the wippen lever 25 and the mount-structure 45 has caused the fly lever proximal end **26*a* and its squared flange 50 to move totally laterally (sidewardly) from supporting contact and from beneath the thrust balancing lever distal end 27*a* and its leather covering pad 42 as the continued lateral movement of the fly lever 26 caused the distal end of the elongated rigid lever 51 to rise upwardly as well as to move further away from the roller 49 such that even greater accentuated pulling (stretching) pressure is exerted on each of the serially connected helical springs 46 and cord 48 such that the resultant force vector 32″ is maximized in its pressure on the roller 50 thereby further depressing the thrust balancing lever proximal end 27*c* such that the thrust balancing lever distal end 27*a* is moved to its highest point; as the thrust balancing lever distal end 27*a* is being moved to its highest point, pressure of the thrust balancing laser is continually decreasing on the supporting fly lever squared flange 50 as the fly lever distal end 26*a* continues to move laterally. As a result of these combined movements upwardly of the thrust balancing lever distal end 27*a* and laterally of the fly lever distal end 26*a*, friction between them at FIG. 2C point 53 (squared corner) is progressively decreasing until friction is near zero at the time that contact therebetween is terminated. The result is a substantially total absence of any discernible friction that might cause a jerking action or an abrupt and high-friction snapping-out of the fly lever distal end 26a from its FIG. 2C state of continued supporting of the thrust lever distal end 27a**.

By tightening (revolving clockwise) the screw 47, the line or cord 48 may thereby be tightened, to thereby cause greater downwardly pressure on the thrust balancing lever end 27b, relieving (reducing) downward pressure of the thrust balancing lever end 27a on the squared portion (squared corner) or flange 53, such that friction would be reduced whenever the fly lever's distal end 26a begins to move laterally away from its supporting position. As above-noted, the fly lever's distal end 26a begins its lateral pivotal movement after the wippen lever 25 has moved upwardly sufficiently for the fly lever's distal end 26c to become abutted against the abutment 36, and as the wippen lever 25 thereafter continues its upward movement when the piano key's proximal end 15a is pushed further downwardly. The reverse adjustment effect may be achieved by loosening the screw 47 by counter-clockwise turning thereof to lessen tension on the line or cord 48.

It is also noted that while solely most preferred embodiments have been herein illustrated, that other embodiments are within the scope of the invention, such as the screw 47 being alternatively mounted on either of support structure 18 or 10, or on a flange extension structure extending upwardly (not shown) from mounting structure 10; the effect of such arrangement would be increased tension on line or cord 48 beginning immediately when the wippen lever distal end 25a begins its upward movement and immediately as and when the downward pressing begins on the piano key proximal end 15a. This would cause immediately a beginning of reduction of downward pressure of the thrust balancing lever end 27a on the squared portion (squared corner) of flange 53. By such an arrangement, lifting action on the thrust balancing lever end 27a does not await (is not delayed until) abutment contact of the fly distal end 26c with the abutment 36.

Likewise, while not illustrated, the scope of the invention includes having the line or cord 48 merely permanently secured solely to the thrust balancing lever end 27b such as to the post or pin 49', such that lateral pivotal movement of fly lever end 26a outwardly (in a direction away from its supporting position of supporting thrust balancing lever end 27) immediately initiates/begins pivotally downward movement of the thrust balancing lever end 27b and the pivotal upward movement of the thrust balancing lever end 27a—at least sufficiently to initiate reduction of pressure of the lever end 27a downwardly on the fly lever's flange 53.

To further understand the prior art and the present invention, it is further noted that historically the purpose of the abutment-stop (more or less equivalent to abutment-stop 36) taken together the presence of a so-called thrust balancing lever (not the direct equivalent of this inventions thrust balancing lever 27), was as follows. The abutment stop prevented the upper pivoting end of the fly lever (equivalent to the present fly lever distal end 26a, except that the prior art fly lever pivotal distal end directly contacted and directly supported the hammer shaft 20 or its contact abutment [equivalent to the present inventions hammer-shaft contact-abutment 44]) from being pushed indefinitely-upwardly where historically it has become jammed against the hammer shaft or its contact-abutment, and when jammed thereby prevented the normal or speedy downward movement of the hammer and its shaft after the hammer had struck the piano string. The subsequent eventual historic insertion of a so-called thrust balancing lever (but historically not supported by the fly lever) that was historically and typically supported by a biasing spring, resulted in a catching of the dropping hammer shaft or its hammer-shaft abutment so as to hold (promptly engage and support) it in a suspended elevated position ready for (susceptable to) a prompt immediate repeat striking (repeat-action), when the piano key is repeatedly restruck)—devoid of having to await total travel of the hammer's lower part downwardly to its normal resting and support position against hammer back-check (equivalent to the present invention's back-check 24).

The invention includes the making of modifications and substitution of equivalents to the extent obvious to a person of ordinary skill in this art.

I claim:

1. In a piano having a base structure means for supporting piano strings and piano keys and structural mechanism thereof for striking strings of a piano, in which structural mechanism thereof includes a balancing rail and a plurality keys pivotably mounted thereon, each key having a key proximal end and a key distal end, of which each key's said distal-end is adapted to abut and to lift a wippen lever pivotably, when a proximate end of the key is pressed downwardly, said structural mechanism including said wippen lever having opposite proximal and distal ends thereof, said wipen lever proximal end being pivotably mounted on said base structure means, and a fly lever having proximal and distal ends thereof and an intermediate portion therebetween, said fly lever intermediate portion being pivotably mounted on said wipen lever distal end, and said structural mechanism further including a thrust balancing lever having balancing lever proximal and distal ends thereof, the thrust balancing lever being pivotably mounted on such that the thrust balancing lever distal end is pivotable upwardly and downwardly alternatively, and said structural mechanism further including a hammer shaft having opposite proximal and distal ends thereof and having a key-striking hammer mounted on said hammer shaft distal end, and said hammer-shaft proximal end being pivotably mounted on said base structure means, such that upward pivotal movement of said wippen lever when said key proximal end is pressed downwardly causes said hammer to move toward and strike one of said piano strings, abutment structure mounted on said base structure means, the improvement comprising in combination, said thrust balancing lever having an intermediate portion between said thrust balancing lever proximal and distal ends, said thrust balancing lever intermediate portion being pivotably mounted on said wippen lever at a first point, said thrust balancing lever distal end resting on and at-least partially supported by said fly lever distal end, said hammer lever intermediate portion resting on said thrust balancing lever distal end, each of said fly lever and said wippen lever having intermediate portions thereof, elongatable resilient means having opposite proximal and distal ends thereof, said abutment structure being positioned such that said fly lever proximal end moves toward and abuts against the abutment structure when said key proximal end is pressed downwardly sufficiently to cause said wippen lever to be thereby raised and to thereby also raise said fly lever, and such that as said wippen lever continues to rise when said fly lever is abutted against said abutment structure, said fly lever pivots on said wippen lever distal end whereby said fly lever distal end moves first upwardly and then pivotably sidewardly away from beneath the thrust balancing lever distal end supported thereon as the fly lever is moved upwardly and correspondingly as the hammer shaft is moved upwardly when the key proximal end is pressed downwardly, said elongatable resilient means distal end being connected to said fly lever at a second point spaced-away from said fly lever proximal end, and said elongatable resilient means proximal end being connected to said wippen lever intermediate portion, said elongatable flexible means distal end being connected to said thrust balancing lever proximal end and being positioned relative to said first point such that said thrust balancing lever proximal end moves downwardly to thereby cause said thrust balancing lever distal end to move upwardly when said fly lever moves sidewardly from beneath said thrust balancing lever distal end.

2. The improvement of claim 1, in which said structural mechanism further includes a change-of-direction means mounted on said thrust balancing lever proximal end, for changing direction of effective resultant pressure thereagainst, said elongatable flexible means being pressed downward against said change of direction means, such that direction of effective resultant pressure against the change-of-direction means moves toward said wippen lever distal end when said wippen lever distal end is raised as a result of said key proximal end being pressed downwardly, and such that effective lifting force of said thrust balancing lever distal end increases as said change of direction means and said thrust balancing lever proximate end move downwardly when said wippen lever distal end moves upwardly during the pressing downwardly of said key proximal end.

3. The improvement of claim 2, in which said fly lever distal end has an irregular shape as viewed in profile view thereof relative to positioning of the fly lever for lateral pivotal movement from beneath and from suport of the distal end of the thrust balance lever distal end, and in which the fly lever distal end includes at-least one flange, such that lateral movement of the fly lever distal end causes said irregularly shaped distal end to further press against said thrust balance lever distal end and thereby moves upwardly said key-striking hammer.

4. The improvement of claim 2, in which the elongatable resilient means comprises a helical spring having opposite proximal and distal ends thereof, and a rigid elongated lever having proximal and distal ends thereof, the rigid elongated lever proximal end being secured rigidly and immovably on said fly lever intermediate portion and said rigid lever distal end being connected to said helical spring distal end, and said helical spring proximal end being connected to said wippen lever intermediate portion, said rigid lever distal end being positioned relative to each of said rigid lever proximal end and said change-of-direction means such that pivotally sideward movement of said fly lever distal end from beneath said thrust balancing lever distal end causes an increase in stretching force on said helical spring with a resulting downward movement of said thrust lever proximal end and upward movement of said thrust lever distal end.

5. The improvement of claim 4, in which said fly lever distal end has an irregular shape as viewed in profile view thereof relative to positioning of the fly lever for lateral pivotal movement from beneath and from support of the distal end of the thrust balance lever distal end, and in which the fly lever distal end includes at-least one flange, such that lateral movement of the fly lever distal end causes said irregularly shaped distal end to further press against said thrust balance lever distal end and thereby moves upwardly said key-striking hammer.

6. The improvement of claim 4, in which said elongated flexible means further includes a substantially non-resilient elongated cord structure having proximal and distal ends and an intermediate portion therebetween, said elongated cord structure distal end being connected to said helical spring proximal end, and said elongated cord structure being connected to said wippen lever intermediate portion, and said elongated cord intermediate portion being in contact and downwardly pressing on said change-of-direction means.

7. The improvement of claim 6, in which said fly lever distal end has an irregular shape as viewed in profile view thereof relative to positioning of the fly lever for lateral pivotal movement from beneath and from support of the distal end of the thrust balance lever distal end, and in which the fly lever distal end includes at-least one flange, such that lateral movement of the fly lever distal end causes said irregularly shaped distal end to further press against said thrust balance lever distal end and thereby moves upwardly said key-striking hammer.

8. The improvement of claim 1, in which said fly lever distal end has an irregular shape as viewed in side profile view thereof relative to positioning of the fly lever for lateral pivotal movement from beneath and from support of the distal end of the thrust balance lever distal end, and in which the fly lever distal end includes at-least one flange, such that lateral movement of the fly lever distal end causes said irregularly shaped distal end to further press against said thrust balance lever distal end and thereby moves upwardly said key-striking hammer.

9. The improvement of claim 1, in which said fly lever distal end has an irregular shape as viewed in side profile view thereof relative to positioning of the fly lever for lateral pivotal movement from beneath and from support of the distal end of the thrust balance lever distal end, and in which the fly lever distal end includes at-least one flange forming said irregularly shaped distal end, such that lateral movement of the fly lever distal end causes said irregularly shaped distal end to further press against said thrust balance lever distal end and thereby moves upwardly said key-striking hammer.

10. The improvement of claim 9, in which said flange forms said fly lever distal end into a substantially squared portion as viewed in said side profile view thereof.

* * * * *